United States Patent [19]
Clark et al.

[11] Patent Number: 5,084,157
[45] Date of Patent: Jan. 28, 1992

[54] GEL ELECTROPHORESIS USING TIME DEPENDENT CONTOUR CONTROLLED ELECTRIC FIELDS

[75] Inventors: Steven M. Clark, Los Angeles; Eric H. Lai, Pasadena, both of Calif.

[73] Assignee: California Institute of Technology, Pasadena, Calif.

[21] Appl. No.: 170,925

[22] Filed: Mar. 21, 1988

[51] Int. Cl.$^5$ ............ G01N 27/26; B01D 57/02
[52] U.S. Cl. .................................. 204/299 R
[58] Field of Search ............... 204/182.8, 299 R; 364/555, 497

[56] References Cited

U.S. PATENT DOCUMENTS

| | | | |
|---|---|---|---|
| 3,562,501 | 2/1971 | Mears | 235/151.35 |
| 4,159,523 | 6/1979 | Neer | 364/571 |
| 4,320,415 | 3/1982 | Jones | 358/105 |
| 4,473,452 | 9/1984 | Cantor | 204/180 G |
| 4,674,323 | 6/1987 | Rulf | 73/61.1 C |
| 4,737,251 | 4/1988 | Carle et al. | 204/182.8 |

OTHER PUBLICATIONS

McPeek, Jr. F. D., et al. "Separation of Large DNA Molecules by Modified Pulsed Field Gradient Gel Electrophoresis" Analytical Biochemistry, 156, pp. 274-285 (1986).

Chu et al., "Separation of Large DNA Molecules by Contour-Clamped Homogenous Electric Fields", Science, vol. 234, p.1583 (1986).

Ellis et al., "Ramped Field Inversion Gel Electrophoresis: A Cautionary Note", Nucleic Acids Research, vol. 15, p. 5489 (1987).

Primary Examiner—John F. Niebling
Assistant Examiner—John S. Starsiak, Jr.
Attorney, Agent, or Firm—Leonard Tachner

[57] ABSTRACT

An apparatus for separating particles within a medium which is capable of generating electric fields having adjustable magnitudes and orientations is disclosed herein. The electrophoretic apparatus of the present invention includes electrode arrangement for providing a plurality of sets of opposing individually responsive electrodes for generating electric fields within the medium, each field having at least one magnitude and direction. The invention further includes a control circuit for selectively controlling electrodes within the electrode sets to vary the magnitudes and directions of the electric fields at locations within the medium. The electric fields induce differing rates of motion of the particles thereby separating the particles.

4 Claims, 5 Drawing Sheets

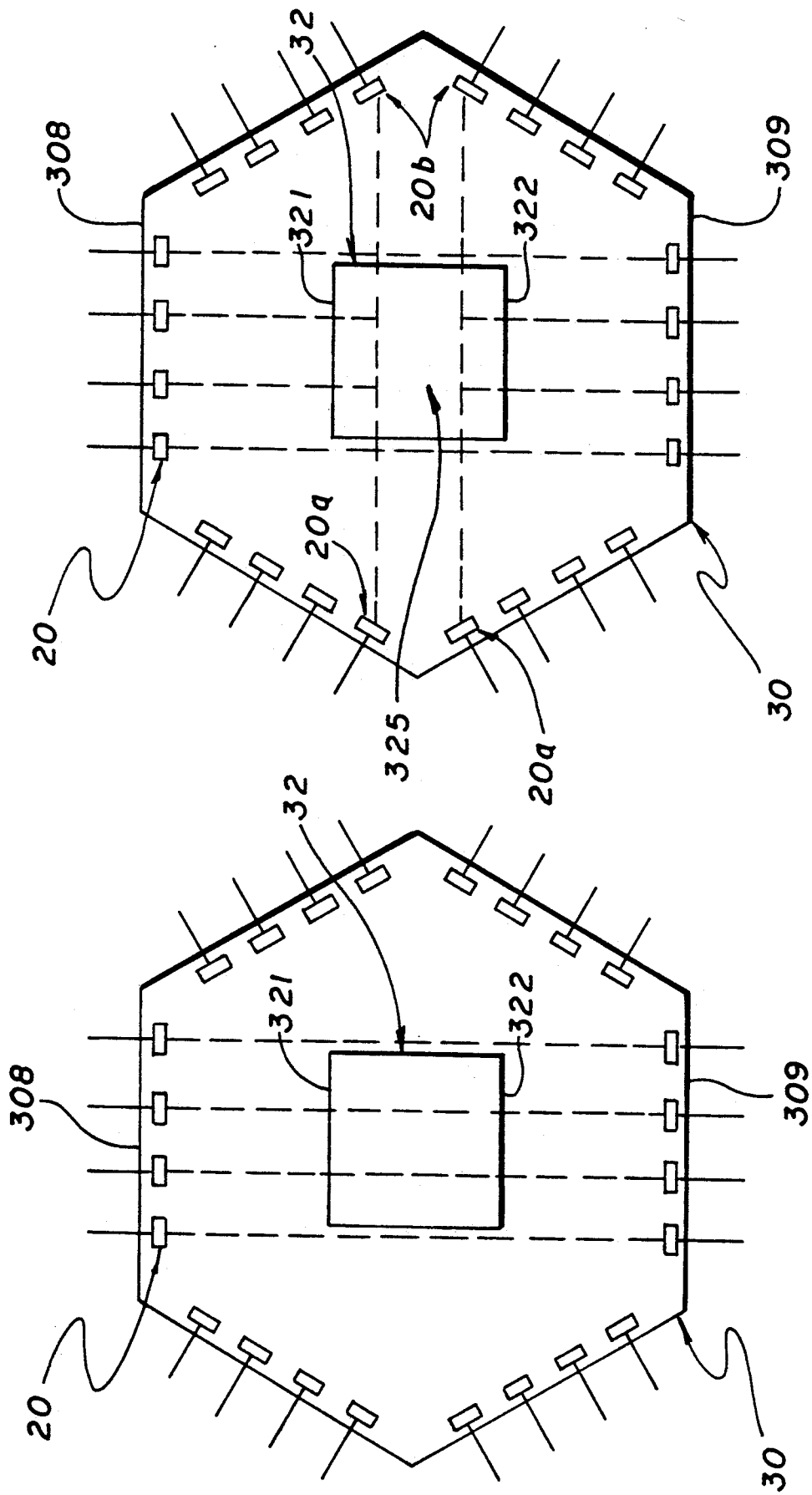

GEL ELECTROPHORESIS USING TIME DEPENDENT CONTOUR CONTROLLED ELECTRIC FIELDS

ORIGIN OF THE INVENTION

The invention described herein was made in the performance of work under a research grant and may be subject to the provisions of Public Law 96-517 (35 U.S.C. 202) under which an election to retain title will be made.

BACKGROUND OF THE INVENTION

1. Field of the Invention

This invention relates to apparatus used to separate molecules according to size. More specifically, this invention relates to the separation of molecules by electrophoresis.

While the present invention is described herein with reference to a particular embodiment for a particular application, it is understood that the invention is not limited thereto. Those having ordinary skill in the art and access to the teachings provided herein will recognize additional embodiments within the scope thereof.

2. Description of the Related Art

The conventional process of electrophoresis has heretofore been used, with limited success, in the separation and size measurement of molecules. The application of gel electrophoresis to DNA molecules has proven useful in sequence analysis, restriction mapping and physical mapping of DNA.

Current methods of electrophoresis typically utilize an electric field to separate charged molecules embedded within a gel matrix. The molecules are separated, within the gel, primarily on the basis of size, charge and physical conformation.

Conventional electrophoresis is performed by an apparatus which generates a unidirectional, uniform electric field provided by a single pair of electrodes. The field produced by such systems is static in that it is time invariant. The charged molecules move within the gel in response to the static field. The mobility of each molecule is related to the logarithm of its molecular weight and the concentration of the gel. Consequently, useful separations of molecules of various sizes have tended to require gels of differing concentrations. Further, insignificant differences in mobility among large macromolecules e.g. DNA molecules in excess of 50,000 base pairs (50 kb) have limited the utility of conventional static field electrophoresis methods as separation tools. That is, prior systems offer limited resolution with respect to large molecules.

The introduction of electrode configurations which generate alternating electric fields transverse to the net direction of macromolecular migration has enabled separation of DNA molecules larger than 50 kb. As disclosed in U.S. Pat No. 4,473,452, issued Sept. 25, 1984 to Schwartz and Cantor, a technique commonly known as pulsed field gradient gel electrophoresis (PFG) employs uniform or non-uniform alternately pulsed electric fields oriented in a predetermined manner to separate molecules.

In "Cell", Vol. 37, May 1984, pp. 67-75, Schwartz and Cantor describe PFG separation of DNA molecules up to 2000 kb, noting that non-uniform electric fields are critical in achieving high resolution. Resolution of DNA fragments separated by PFG is typically a function of the pulse time, geometry and strength of applied electric fields. However, point electrode elements typically utilized in conventional PFG devices are often capable of assuming only a pair of electric potentials thus constraining the range of fields which may be applied to a gel.

Though PFG electrophoresis enables separation of larger DNA macromolecules than conventional static field approaches, the qualitative usefulness of PFG separations generated by non-uniform electric fields has been limited by the production of curved trajectory migrations. That is, as a result of the application of typically non-uniform, spatially nonhomogenous electric fields in PFG electrophoresis, DNA samples will typically follow nonlinear paths. As is known in the art, comparisons between the migrations of known and unknown samples are typically more accurate when the trajectories of both samples are linear rather than nonlinear.

In "Analytical Biochemistry", Vol. 156, 1986, pp. 274-285, McPeek describes a technique of using alternately pulsed, opposing nonhomogenous fields to counteract the effect of "lane bending" (curved migration trajectories). This approach improved linearity in the electrophoretic migration path, but the conventional bistable point electrode configurations utilized allow only limited control of electric fields.

An alternative approach developed to achieve improved linearity in electrophoretic migration is known as field inversion (FI) gel electrophoresis. In FI electrophoresis the applied electric field is periodically inverted for unequal intervals using a pair of conventional electrodes with net migration of a sample occurring in the field direction associated with the longer interval. The opposing electric fields in FI electrophoresis are said to have a "reorientation angle" of 180 degrees while the reorientation angle in conventional PFG electrophoresis is typically between 90 to 150 degrees. With periodic switching between electric fields, FI electrophoresis has produced separation of DNA in the 10 kb to 1600 kb size range. Resolution of DNA up to 750 kb has been better in FI electrophoresis than in conventional PFG electrophoresis.

Despite offering improved resolution of certain DNA size ranges relative to PFG electrophoresis, conventional FI electrophoresis typically does not induce a monotonic relationship between migration mobility and molecular weight. Specifically, in FI electrophoresis molecules differing in size by several times may exhibit similar net migration in the direction of separation. In some instances this limitation has been partially overcome by linearly increasing/decreasing the duration of the applied field pulses as a function of time (switch time ramping).

Electrophoretic separation by contour-clamped homogenous electric fields (CHEF) has recently been utilized to separate DNA in excess of 2000 kb with generally improved resolution relative to PFG or FI electrophoresis. See "Science", Vol. 234, Dec. 19, 1986, pp. 1582-1585 by Chu et al. The apparatus used includes multiple electrodes evenly spaced along a polygonal contour. Electrodes on opposite sides of the polygon may be utilized to define the electric field orientation within an electrophoretic gel. Electrodes on the remaining sides of the polygon are linked by equal resistors and hence have associated intermediate potentials. These intermediate potentials are equivalent to the potentials which would exist at the position occupied by the intermediate electrode in a completely homogenous field. The field is typically periodically switched between two pairs of electrodes on opposing sides of the polygon with the potentials of the intermediate electrodes on remaining sides of the polygon also adjusted accordingly. Field homogeneity within the gel allows expedient comparison between samples in different regions of a single gel as each sample experiences a substantially equivalent field.

While this technique provides more effective separation of certain large DNA macromolecules than that afforded by conventional PFG or FI electrophoretic techniques, the particular CHEF electrophoresis scheme proposed by Chu et al. has two primary limitations. First, the electric field reorientation angle is effectively defined by, and restricted to, the geometry of the electrode configuration. For example, as noted by Chu on page 1583 of the above-noted reference, a square electrode configuration produces a 90 degree reorientation angle while a hexagonal electrode configuration may generate reorientation angles of either 60 or 120 degrees. This constraint on reorientation angles may limit the utility of conventional CHEF electrophoresis. Hence, the reorientation angles or combinations thereof necessary for optimum separation of DNA within given size ranges may be unattainable with the apparatus and teaching of Chu.

Second, the system of Chu is generally limited to the production of a fixed magnitude field during the electrophoretic process. This constant field magnitude can be disadvantageous as utilizing electric fields with magnitude gradients may aid in separation of desired DNA size ranges.

As a result of the above limitations, conventional CHEF electrophoretic systems are typically capable of generating only two "field states". That is, the electric fields produced during CHEF electrophoresis are of fixed magnitude and are usually constrained to alternate in two directions. Thus, potentially improved methods of electrophoretic separation requiring generation of more than a pair of field states could generally not be implemented using conventional CHEF systems.

Hence a need in the art exists for an electrophoretic apparatus for separating particles within a medium which is capable of generating electric fields having adjustable magnitudes and orientations.

SUMMARY OF THE INVENTION

The need in the art for an apparatus for separating particles within a medium which is capable of generating electric fields having adjustable magnitudes and orientations is addressed by the present invention. The electrophoretic apparatus of the present invention includes [electrode means for providing] a plurality of sets of opposing individually responsive electrodes for sequentially generating electric fields within the medium, each field having at least one magnitude and direction. The invention further includes [means] control circuitry adapted to individually activate the electrodes for selectively controlling electrodes within the electrode sets to vary the magnitudes and directions of the electric field at locations within the medium. The electric fields induce differing rates of motion of the particles thereby separating the particles.

BRIEF DESCRIPTION OF THE DRAWINGS

FIG. 3a provides a first illustrative example of a localized electric field gradient generated by individual control of the electrodes by the apparatus of the present invention.

FIG. 3b provides a second illustrative example of a localized electric field gradient generated by individual control of the electrodes by the apparatus of the present invention.

DESCRIPTION OF THE INVENTION

Figure 1:
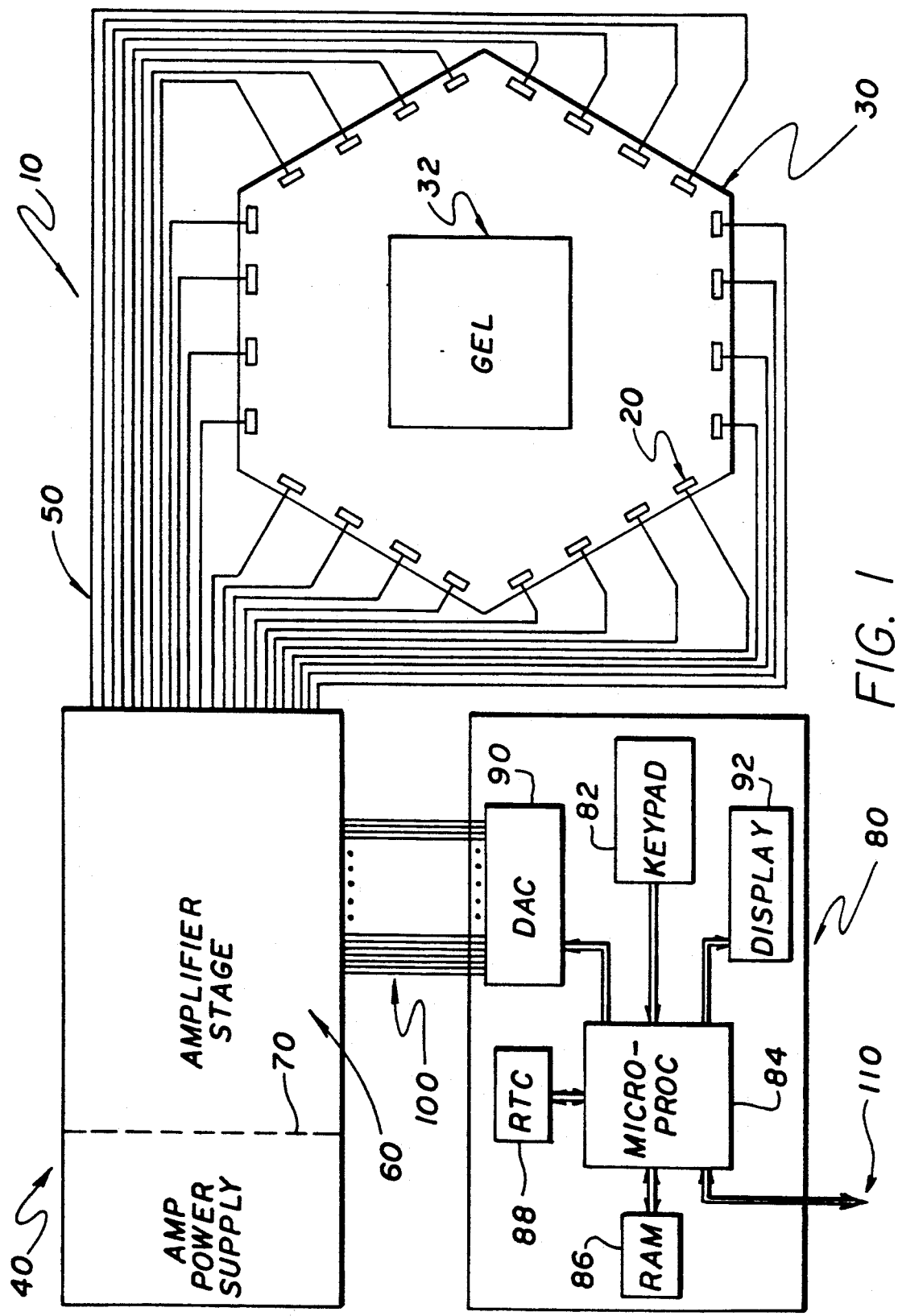
FIG. 1 is an illustrative block diagram representation of a preferred embodiment of the electrophoretic apparatus of the present invention.

As shown in FIG. 1, an illustrative embodiment of the electrophoretic apparatus 10 of the present invention includes twenty four electrodes 20 suspended within the periphery of a hexagonal buffer container 30. Connecting lines 50 couple the electrodes 20 to a driver module 40. The driver module 0 is linked to a control module 80 by a plurality of signal lines 100. A computer (not shown) may communicate with the control module 80 via an I/O port 110.

As described more fully below, the driver module 40 impresses potentials individually upon the electrodes 20. A buffer solution is enclosed by the buffer container 30 and surrounds a gel 32. The buffer solution conducts electrical current from the electrodes 20 which sets up an electric field in the gel 32. Molecules of different sizes move at different rates through the gel 32 in response to electric fields generated by the electrodes 20. These differing velocities induce separation of molecules within the gel 32. The control module 80 provides analog signals via the lines 100 to the driver module 40 indicative of the potentials to be impressed on the electrodes 20. An operator may select the order and duration of various electric field states to be applied to the gel 32 via a keypad 82. Alternatively, digital instructions specifying generation of a particular electric field may be obtained from an external computer through an I/O port 110.

The buffer container 30 generally will be made from a material such as Plexiglas and will typically contain an ionic buffer used in conventional electrophoresis e.g. 45 mM Tris-borate, 2 mM EDTA, pH 8.0. The buffer may be recirculated through the container 30 with a pump and temperature controlled reservoir (not shown) to maintain a constant temperature within the container 30.

The gel 32 is mounted conventionally within the container 30. The gel 32 typically consists of a 0.4 to 2.0% agarose gel generally having a thickness on the order of less than 1 cm. A linear array of sample wells are cast along one side of the gel 32 using a Plexiglas comb in a manner familiar to one skilled in the art. Agarose plugs containing DNA or other material to be separated are placed into the sample wells within the gel 32 prior to filling the container 30 with buffer solution.

The electrodes 20 each comprise a 0.030" diameter piece of platinum wire approximately 0.650" in length held in place by an insulating material e.g. Plexiglas. Holes may be included in the sides of the container 30 to facilitate electrical connection of the electrodes 20 to the driver module 40 via the lines 50.

Arrangement of the electrodes 20 in a closed contour allows control of the electric field within the gel 32, wherein potential gradients in a selected vectorial sum direction can be established by virtue of which of electrodes 20 are energized.

Increases in the number of electrodes 20 included along a contour surrounding the gel 32 will typically allow, if desired, generation of a more homogenous electric field, that is to say that the distribution of electric field lines is more uniform. However an arrangement as in FIG. 2 including twenty-four electrodes 20 and gel 32 having transverse dimensions of approximately 13 cm × 13 cm provided, to a first order approximation, a homogenous electric field in experimental trials.

Figure 2:
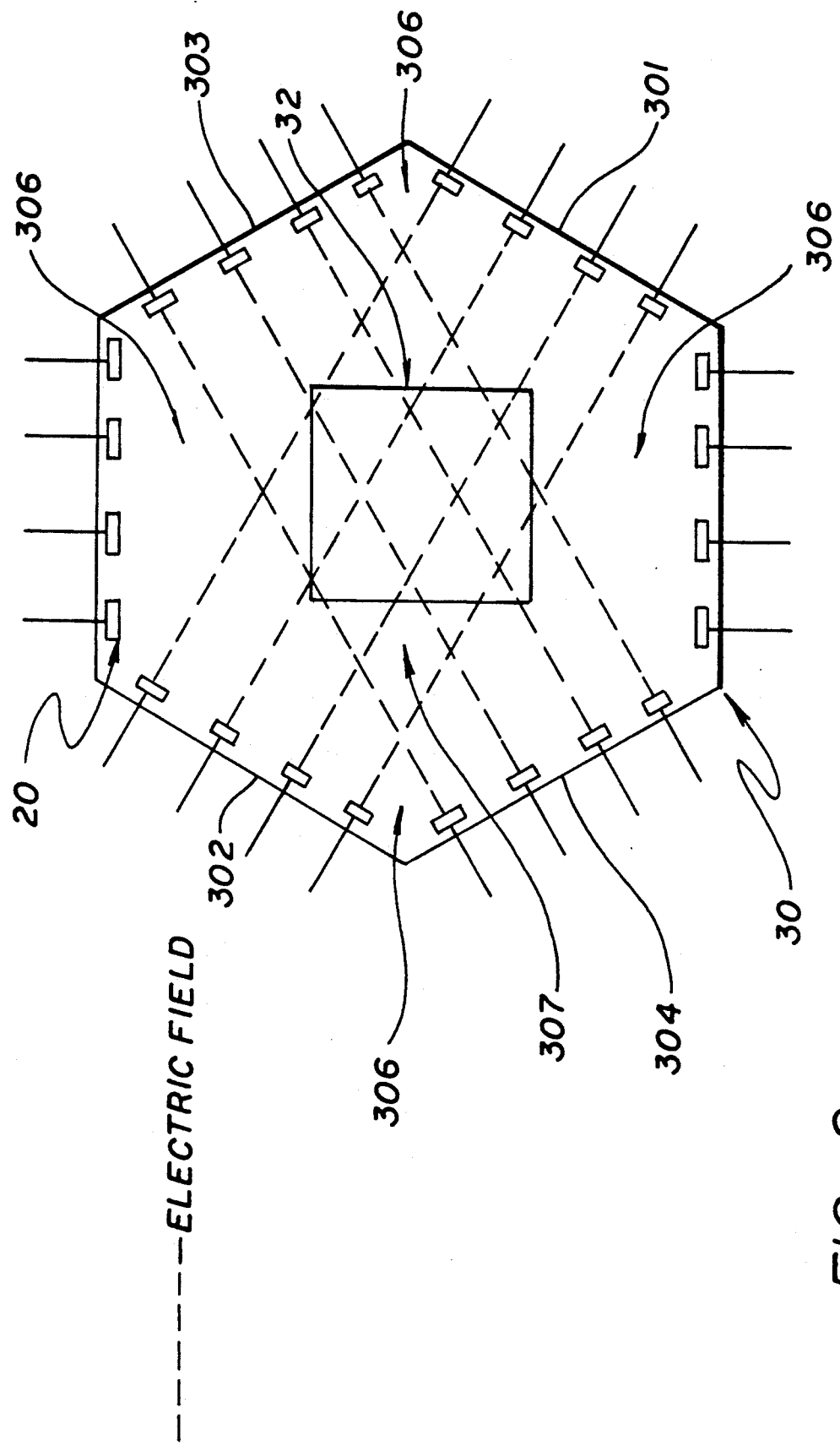
FIG. 2 shows a pair of electric fields generated by the electrodes of the present invention suspended within the buffer container.

FIG. 2 illustrates a specific, nonlimiting case in which the electrodes 20 generate a pair of homogenous fields. A first electric field is generated by the sets of electrodes 20 bordering a pair of sides 301 and 302 of the container 30. Similarly, a second electric field is produced by the sets of electrodes 20 bordering a pair of sides 303 and 304 of the container 30. The first and second electric fields are alternately applied to the gel 32. The gel 32 is positioned within an active region 307 in which both the first and second electric fields are substantially homogeneous. Hence molecules within the gel 32 are subjected to homogenous fields. Nonhomogenous fields, those with a non-uniform distribution of electric field lines, within the inactive regions 306 do not affect migration of molecules within the gel 32.

Individual control of the electrodes 20 allows both the magnitude and vectorial sum direction of electric fields impressed upon specific regions of the gel 32 to be varied throughout an electrophoretic process. FIGS. 3a and 3b are useful in illustrating a specific example of the flexibility in electric field generation afforded by individual control of the electrodes 20. In FIG. 3a a sample of molecules to be separated is loaded as described previously near an edge 321 of the gel 32. An electric field may initially be applied by the electrodes 20 bordering the walls 308 and 309 of the container 30 which will move the molecules toward the edge 322. In order to increase the resolution (separation) of molecules within a given size range it may be advantageous to apply an alternating, transverse electric field for a specific time interval within the region 325 via the electrodes 20a and 20b as shown in FIG. 3b. In this manner temporary application of an alternating electric field within a specific region of the gel 32 may allow greater resolution of a particular size range of the molecular sample. The lack of individual control of electrodes within prior art systems has prevented application of similar temporary, controlled field gradients within localized regions.

Figure 3C:
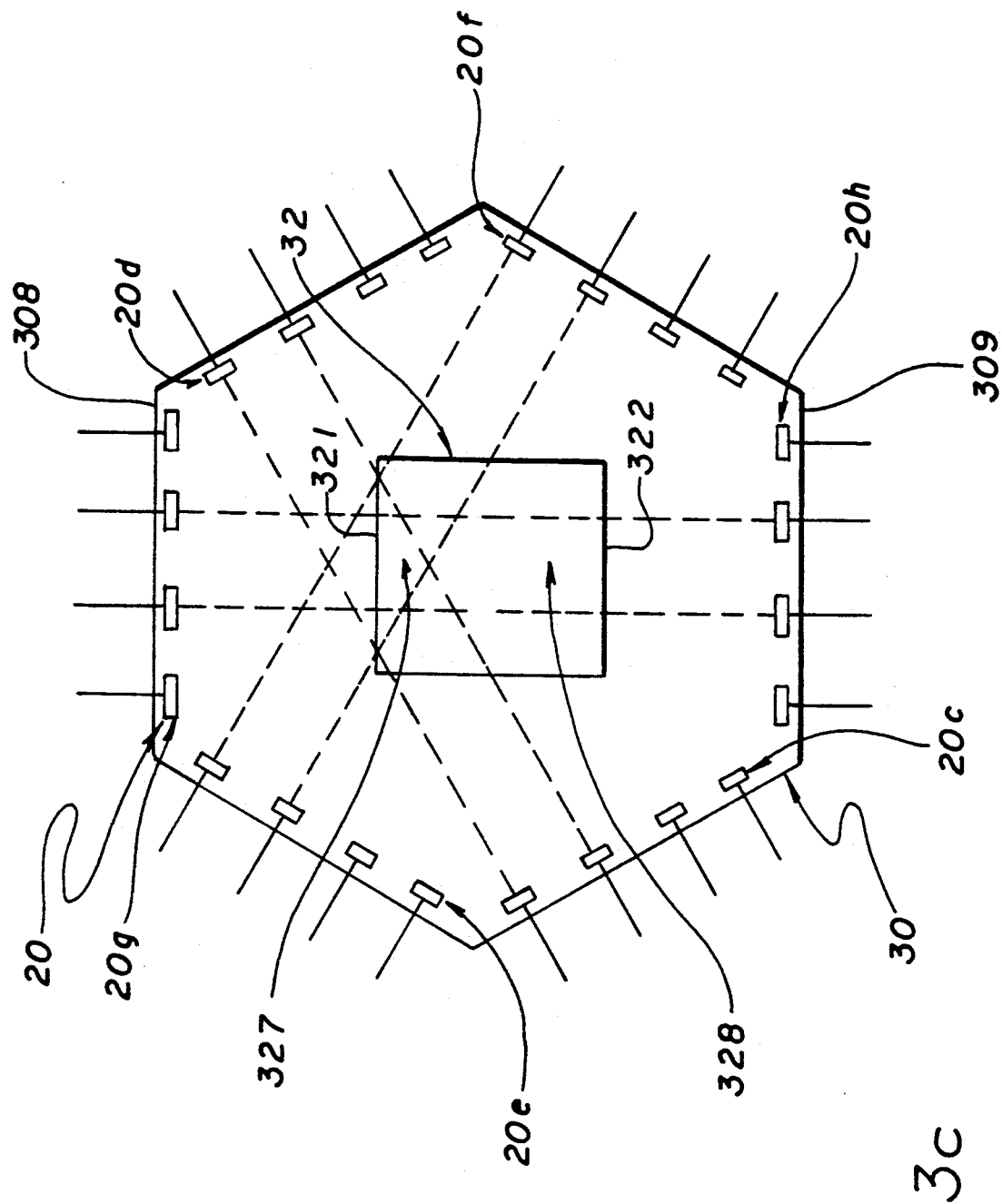
FIG. 3c illustrates an electrophoretic process during which the electrodes of the apparatus of the present invention provide three independent electric fields.

FIG. 3c illustrates a mode of operation of the electrophoretic apparatus 10 of the present invention wherein three electric fields are independently applied to the gel 32. These three fields are generated primarily by the sets of electrodes 20c, 20d, 20e, 20f, 20g and 20h. Consider for example a molecular sample loaded as described previously near the edge 321 of the gel 32. The field generated by the electrodes 20g and 20h may initially be applied until a first portion of the sample has migrated to a region 327 while a second portion of the sample has migrated to a region 328. Following this initial migration further separation of molecules within the region 327 may in some instances be enhanced through application of transverse, alternating fields via the electrodes 20c, 20d, 20e, and 20f. In this manner controlled field gradients are provided within specific regions of the gel 32 for desired time intervals. In contrast, known prior art systems are typically unable to vary the combination of fields applied to localized regions (e.g. regions 327 and 328) for specified intervals during a separation process.

Figure 4:
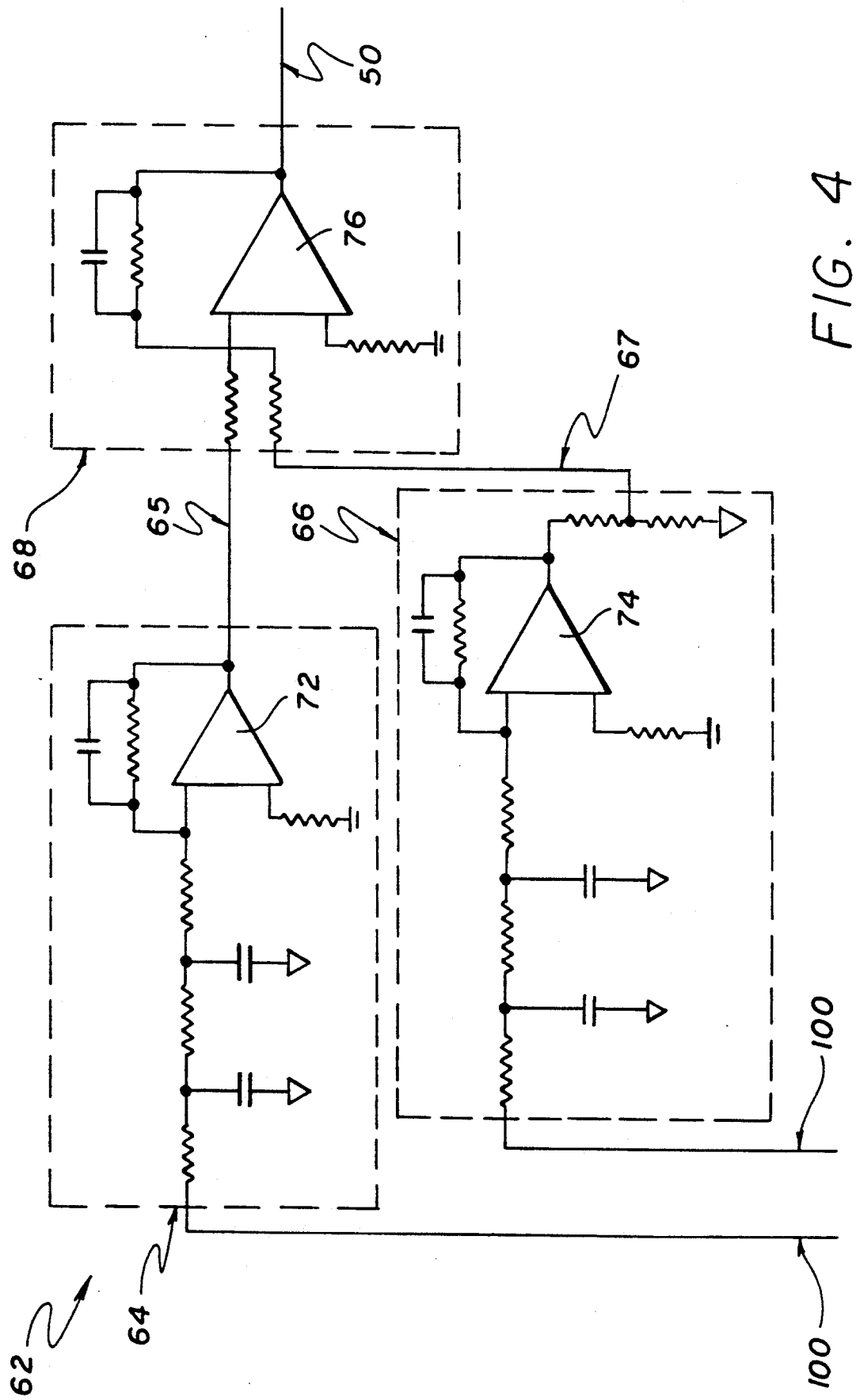
FIG. 4 is a schematic representation of one of the three element electrode amplifiers included in a preferred embodiment of the amplifier stage of the apparatus of the present invention.

The driver module 40 includes an amplifier stage 60 and an amplifier power supply 70. The amplifier stage 60 includes twenty-four three-element amplifiers 62 (see FIG. 4) each connected by one of the lines 50 to one of the electrodes 20. The amplifier power supply 70 comprises two individual power supplies which energize the three element amplifiers 62. As shown in FIG. 4, each of the three element amplifiers 62 include first, second and third op-amp circuits 64, 66, 68.

The first op-amp circuit 64 amplifies an analog signal representing the most significant byte (MSB) of a digital control word. The control word is indicative of a potential to be impressed on one of the electrodes 20 and is received from the control module 80 via a line 100. The amplified analog signal representing the MSB appears on the line 65. In a preferred embodiment appropriate resistive and capacitive elements are coupled to the operational amplifier 72 such that the first op-amp circuit 64 exhibits a 3 dB roll-off point of approximately 1 kHz.

The second op-amp circuit 66 amplifies an analog signal representing the least significant byte (LSB) of a digital control word. The control word is indicative of a potential to be impressed on one of the electrodes 20 and is received from the control module 80 via a line 100. The amplified analog signal representing the LSB appears on the line 67. In a preferred embodiment appropriate resistive and capacitive elements are coupled to the operational amplifier 74 such that the second op-amp circuit 66 exhibits a 3 dB roll-off point of approximately 1 kHz.

The amplified analog representations of the MSB and the LSB are carried to the third op-amp circuit 68 by the lines 65 and 67. The third op-amp circuit 68 combines and amplifies these MSB and LSB signals present on the lines 65 & 67. The output of the third op-amp circuit 68 appears as a voltage on the line 50 which is impressed upon one of the electrodes 20. In a preferred embodiment appropriate resistive and capacitive elements are coupled to a an operational amplifier 76 such that the third op-amp circuit 68 exhibits a 3 dB roll-off point of approximately 1 kHz.

Referring again to FIG. 1 the control module 80 includes a keypad 82, a microprocessor 84 with associated random access memory (RAM) 86, a real time clock (RTC) 88, a display 92, and a multi-channel digital to analog converter (DAC) 90. The DAC 90, RTC 88, microprocessor 84 and RAM 86 are typically mounted and interconnected on a printed circuit board in a conventional manner. The display 92 generally comprises a DC plasma display module.

In the embodiment of FIG. 1 the DAC 90 is comprised of 48 individual digital to analog converters as well as a latch register (not shown). In a specific mode of operation described below the RAM 86 stores digital control words which specify electric field states to be generated by the electrodes 20. The microprocessor 84 controls the DAC 90 by sending these digital control words to the latch register associated with the DAC 90. The 48 individual digital to analog converters within the DAC 90 are then simultaneously actuated and convert the digital words to analog signals. These analog signals are sent to the driver module 40 via the lines 100.

In a first mode of operation sixteen bit digital control words comprising an eight bit most significant byte (MSB) and an eight bit least significant byte (LSB) are stored in RAM 86. The digital control words contain information pertaining to the magnitude and timing of application of potentials impressed upon the electrodes 20 by the driver module 40. For example, the control words typically will specify imposition of a particular electric field (state) upon the gel 32 for a specified time interval by indicating appropriate potentials to be impressed on the electrodes 20. Information relating to the timing and sequence of the above field states is entered through the keypad 82.

A second mode of operation utilizes a computer (not shown) which communicates with the control module 80 through the I/O port 110. As mentioned above, the voltages present on the electrodes 20 are determined by the particular field state being impressed upon the gel 32. In the second mode of operation the computer (under the direction of a computer program) calculates the voltages on the electrodes 20 necessary to generate field states of specified magnitude and direction. These electrode voltages, as well as the timing and sequence of application of the field states, are stored in the memory of the computer and accessed during execution of the computer program. The duration of application of the field states upon the gel 32 is either fixed or programmed to linearly increase/decrease during the electrophoretic separation process. In actual operation the computer program initially calculates values corresponding to each field state to be sent to the DAC 90. These field state values are recalled as the program loops with the assistance of the RTC 88 and a timer (not shown). Similarly, a computer display (not shown) is updated during the separation process to reflect the voltages associated with each of the electrodes 20 in a particular electric field state.

The durations and sequences of the electric field states may be chosen to evenly separate molecules within a given size range or to increase the resolution of molecules of particular sizes within a given range. In this manner the second mode of operation allows programming of field states suitable for desired resolution of particular molecular size ranges.

Additionally, in the second mode of operation the electrophoretic apparatus 10 of the present invention may be used to simulate previously described electrophoresis apparatus e.g. PFG, FI, CHEF or combinations thereof. Specifically, the individual control of the electrodes 20 allows generation of substantially all electric field patterns associated with prior methods of electrophoretic separation disclosed herein. Further, this simulation capability may allow generation of the electric fields comprising novel electrophoretic separation techniques with appropriate programming of the computer. Hence, the present invention may in some instances obviate the need for constructing separate electrophoretic devices to test alternate field patterns.

The present invention has been described with reference to a particular planar hexagonal electrode configuration. It is understood that the invention is not limited to the arrangement of the electrodes 20. Other two-dimensional contours (e.g. circular) or three-dimensional configurations may be used without departing from the scope thereof. It is also understood that the circuitry disclosed for impressing potentials on the electrodes 20 may be modified without departing from the scope of the invention.

It is also noted the apparatus 10 is not designed solely for the separation of a particular type of macromolecule e.g. DNA. With access to the teachings of this invention, it may be obvious to one of ordinary skill in the art to electrophoretically separate other nucleic acids, proteins or substances not specifically mentioned herein. It is contemplated by the appended claims to cover these and any other such modifications.

Accordingly, what is claimed is:

1. An electrophoretic apparatus for separation of particles within a medium comprising:
    a container having a polygonal perimeter contour for supporting said medium therein;
    a plurality of electrodes positioned along said polygonal contour for generating an electric field within said medium responsive to an energizing potential applied between at least two of said plurality of electrodes;
    a buffer solution disposed intermediate said medium and said plurality of electrodes, said buffer solution being in contact with both said medium and said plurality of electrodes for conduction of an electric current therethrough;
    a plurality of amplifier circuits connected to said electrodes for impressing said energizing potential upon said electrodes;
    memory means for storing digital control words;
    microprocessor means coupled to both said memory means and said plurality of amplifier circuits for controlling said plurality of amplifier circuits responsive to said digital control words;
    a digital-to-analog converter connected between said microprocessor means and said amplifier circuits for converting digital impulses from said microprocessor means into analog signals for input to said amplifier circuits; and
    interface means coupled to said microprocessor means for entering said control words in said memory means.

2. An electrophoretic apparatus for the separation of particles within a medium comprising:
    a support for said medium in which said particles are separated;
    a buffer solution surrounding said medium within said support;
    a plurality of pairs of opposing electrodes disposed about a perimeter portion of said support in contact with said buffer solution;
    drive means coupled to said plurality of electrode pairs for application of an energizing potential to at least one of said plurality of pairs of electrodes, said drive means including a plurality of output lines for coupling to said plurality of electrode pairs, each of said plurality of output lines being coupled to a respective one of said electrodes of said plurality of electrode pairs for individual energization thereof;
    control means coupled to said drive means for selecting and sequentially changing which of said electrode pairs receive said energizing potential, said control means including means for selectively changing a magnitude of said energizing potential being applied to said electrode pairs, whereby a selected number of said electrode pairs are selected to receive said energizing potential while remaining electrode pairs remain de-energized.

3. The electrophoretic apparatus as recited in claim 2 where said drive means includes a plurality of amplifier circuits, each of said plurality of amplifier circuits being coupled to a respective one of said plurality of pairs of electrodes for said individual energization thereof.

4. The electrophoretic apparatus as recited in claim 3 where said control means includes microprocessor means coupled to said plurality of amplifier circuits for programmably selecting (1) which of said electrode pairs are energized, (2) a magnitude for said energizing potential, and (3) a sequence for changing which of said electrode pairs are energized.

* * * * *